United States Patent
Tatsuzaki et al.

(10) Patent No.: US 10,889,557 B1
(45) Date of Patent: Jan. 12, 2021

(54) METHOD OF PRODUCING AN ALKOXYFLAVONE DERIVATIVE

(71) Applicant: Tokiwa Phytochemical Co., Ltd., Sakura (JP)

(72) Inventors: Jin Tatsuzaki, Sakura (JP); Tsutomu Ishikawa, Sakura (JP)

(73) Assignee: TOKIWA PHYTOCHEMICAL CO., LTD., Sakura (JP)

( * ) Notice: Subject to any disclaimer, the term of this patent is extended or adjusted under 35 U.S.C. 154(b) by 0 days.

(21) Appl. No.: 16/727,457

(22) Filed: Dec. 26, 2019

(51) Int. Cl.
*C07D 311/30* (2006.01)

(52) U.S. Cl.
CPC .................. *C07D 311/30* (2013.01)

(58) Field of Classification Search
CPC ..................................... C07D 311/30
USPC .................................. 549/403, 399
See application file for complete search history.

(56) References Cited

PUBLICATIONS

Tatsuzaki et al.: A simple and effective preparation of quercetin pentamethyl ether from quercetin. Beilstein J. of Org. Chem., vol. 14, pp. 3112-3121, 2018.*

Metabolism-based synthesis, biologic evaluation and Sars analysis of O-methylated analogs of quercetin as thrombin inhibitors, by Zhi-Hao Shi et al, European Journal of Medicinal Chemistry, vol. 54, 2012, pp. 210-222 (13 pages).
Synthesis of alkyl quercetin derivatives, by M. Kim et al, J. Korean Society for Applied Biological Chemistry, vol. 58., 2015, pp. 343-348 (6 pages).

\* cited by examiner

*Primary Examiner* — Charanjit Aulakh
(74) *Attorney, Agent, or Firm* — Flynn Thiel, P.C.

(57) ABSTRACT

A method of producing an alkoxyflavone derivative involves a step of reacting hydroxyflavone derivative which is shown in the below chemical formula and dialkyl sulfate in the presence of dimethyl sulfoxide and an alkali hydroxide. Further, in the chemical formula below, $R_{11}$-$R_{14}$, $R_{21}$-$R_{25}$ and $R_3$ are independently one of hydrogen, hydroxyl group, ester group, alkoxy group, alkylenedioxy group, sulfonyl group and alkyl group, respectively. However, at least two of $R_{21}$-$R_{25}$ and $R_3$ are hydroxyl groups.

Chemical Formula 1

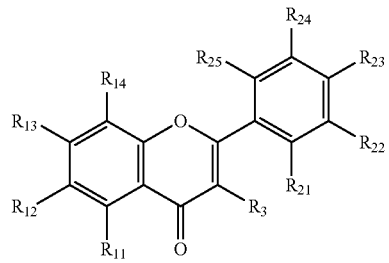

3 Claims, No Drawings

METHOD OF PRODUCING AN ALKOXYFLAVONE DERIVATIVE

TECHNICAL FIELD

The present invention relates to a method of producing an alkoxyflavone derivative.

RELATED ART

Hydroxyflavone derivatives, which have a flavone skeleton which has hydroxyl groups, are found widely in plants, and it is known that they exhibit various bioactivities, respectively.

For example, quercetin (3,5,7,3',4'-pentahydroxyflavone), which is one of the hydroxyflavone derivatives, is the chief ingredient of onions.

More, alkoxyflavone derivatives, in which the hydroxyl groups of the hydroxyflavone derivatives are substituted to the alkoxy groups, are also found widely in plants, and it is also known that they exhibit various bioactivities, respectively.

For example, in black turmeric (*Kaempferia parviflora*), there exists 3,5,7,3',4'-pentaalkoxyflavone in which the five hydroxyl groups of quercetin are substituted to alkoxy groups.

And it is known that the 3,5,7,3',4'-pentaalkoxyflavone exhibits anti-saccharification activity against saccharification, which is one of the causes of aging.

Thus, presently, it is tried to synthesize the alkoxyflavone derivatives from the hydroxyflavone derivatives.

For example, the trials are described in the below-identified non-patent document 1 and 2.

REFERENCE FOR RELATED ART

Non-Patent Document

NON-PATENT DOCUMENT 1 Shi, Z.-H et al., Eur. J. Med. Chem., 2012, 54, 210-222.
NON-PATENT DOCUMENT 2 Kim, M. et al., J. Korean Soc. Appl. Biol. Chem., 2015, 58, 343-248.

DESCRIPTION OF THE INVENTION

Solution to the Problems

However, in the above-described non-patent document 1, there remains the problem that not all hydroxyl groups of the hydroxyflavone derivatives are substituted to alkoxy groups. Namely, the byproduct, in which there remain some hydroxyl groups, will be produced.

In contrast, the above-described non-patent document 2 discloses that a compound in which all hydroxyl groups of hydroxyflavone derivative were substituted to alkoxy groups. However, the yield is low.

Thus, concerning the above-described problems, the object of the present invention is to provide a method of producing alkoxyflavone derivative with high yield, in which all hydroxyl groups of hydroxyflavone derivative are substituted to alkoxy groups with high yield.

Means for Solving the Problems

One aspect of the present invention which solves the above-described problems is a method of producing an alkoxyflavone derivative, which comprises a step of reacting a hydroxyflavone derivative which is shown in the below chemical formula and dialkyl sulfate in the presence of dimethyl sulfoxide and alkali hydroxide.

Chemical Formula 1

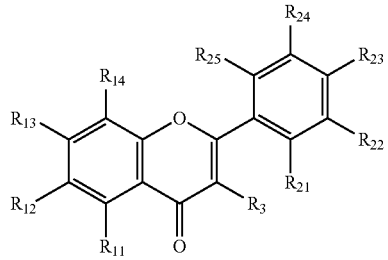

Further, in the above-described chemical formula, $R_{11}$-$R_{14}$, $R_{21}$-$R_{25}$ and $R_3$ are independently one of hydrogen, hydroxyl group, ester group, alkoxy group, alkylendioxy group, sulfonyl group and alkyl group, respectively. However, at least two of $R_{11}$-$R_{14}$, $R_{21}$-$R_{25}$ and $R_3$ are hydroxyl groups.

Effects of the Invention

Therefore, by the present invention, it is possible to provide a method of producing alkoxyflavone derivatives, in which the all hydroxyl groups of hydroxyflavone derivatives are substituted to alkoxy groups, with high yield.

BEST MODE FOR CARRYING OUT THE PRESENT INVENTION

Hereafter, the embodiment of the present invention is described below in detail.

However, the present invention can be carried out with various embodiments and is not limited to the embodiment described below.

One aspect of the present invention is a method of producing an alkoxyflavone derivative, which comprises a step of reacting a hydroxyflavone derivative which is shown in the below chemical formula and a dialkyl sulfate in the presence of dimethyl sulfoxide and an alkali hydroxide.

Chemical Formula 2

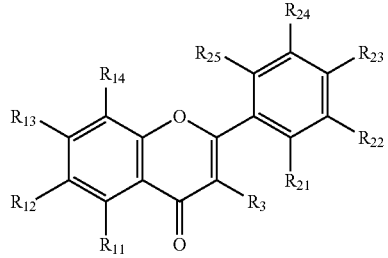

Further, in the above-described chemical formula, $R_{11}$-$R_{14}$, $R_{21}$-$R_{25}$ and $R_3$ are independently one of hydrogen, hydroxyl group, ester group, alkoxy group, alkylendioxy group, sulfonyl group and alkyl group, respectively. However, at least two of $R_{11}$-$R_{14}$, $R_{21}$-$R_{25}$ and $R_3$ are hydroxyl groups.

In this producing method, "hydroxyflavone derivative" means a compound that has a flavone skeleton and bound hydroxyl groups.

Hydroxyflavone derivatives exist a lot in plants and many of them have characteristic bioactivities, respectively.

In this producing method, it is desirable that the hydroxyflavone derivative is obtained by extracting it from plants or synthesizing it artificially.

In the hydroxyflavone derivative of this producing method, when at least one of the above-described substituents which are expressed as $R_{11}$-$R_{14}$, $R_{21}$-$R_{25}$, and $R_3$ is an alkoxy group, it is desirable that the number of carbons is not less than 1 and not greater than 5.

As examples of the alkoxy groups include, but are not limited to, methoxy group, ethoxy group, propoxy group, butoxy group, pentoxy group, and benzyloxy group.

More, also in the case of the alkyl group, it is desirable that the number of carbons is not less than 1 and not greater than 5.

The examples of the alkyl group include, but are not limited to, methyl group, ethyl group, propyl group, butyl group, and pentyl group.

More, also in the case of the carboxy group, it is desirable that the number of carbons is not less than 1 and not greater than 5.

More, in the case of the ester group or sulfonyl group, it is desirable that the number of carbons that are included in the terminated functional group is not less than 1 and not greater than 5. The examples of the groups include, but are not limited to, methyl group, ethyl group, propyl group, butyl group, pentyl group, and benzyl group.

More, in the case of the alkylendioxy group, it is desirable that it is the group that comprises the adjacent two functional groups which are connected via an oxygen atom. And it is desirable that the number of carbons is not less than 1 or 2, for example, it is a methylenedioxy group or an ethylenedioxy group.

More, it is desirable that the hydroxyflavone derivative is 3-hydroxyflavone, 5,7,4'-trihydroxyflavone (apigenin), 5,7,3',4'-tetrahydroxyflavone (luteolin), 3,5,7,4'-tetrahydroxyflavone (kaempferol), 3,5,7,3',4'-pentahydroxyflavone (quercetin), or 3,5,7,3',4',5'-hexahydroxyflavone (myricetin). But it is not limited to them, as long as it has the above-described structure.

More, in this producing method, the dimethyl sulfoxide ($C_2H_6SO$, DMSO) works as a solvent which can solve the hydroxyflavone derivative and the dialkyl sulfate.

In this producing method, the amount of DMSO which is used in this method is not limited as long as the above-described effect is available. For example, when the amount of the hydroxyflavone derivative is assumed to be 1 mol, it is desirable that the amount of DMSO is not less than 500 mL and not greater 5000 mL. It is more desirable that it is not less than 750 mL and not greater than 3500 mL, and it is further desirable that it is not less than 1200 mL and not greater than 2400 mL.

More, the dialkyl sulfate which is used in this method is used as a source of alkyl groups.

Here, it is desirable that the alkyl group of the dialkyl sulfate contains at least one of methyl, ethyl, propyl, butyl, and pentyl. Practically, it is desirable that the alkyl group contains at least one of dimethyl sulfate, diethyl sulfate, dipropyl sulfate, dibutyl sulfate, and dipentyl sulfate.

In this producing method, the amount of the dialkyl sulfate is properly adjustable as long as it is possible to substitute the hydroxyl group in hydroxyflavone derivatives to the alkoxy group.

For example, when the amount of the hydroxyl group of the hydroxyflavone derivative is assumed to be 1 mol, it is desirable that the amount of the dialkyl sulfate is not less than 1 mol. It is more desirable that it is not less than 1 mol and not greater than 3 mol, and further desirable that it is not less than 1.5 mol and not greater than 2 mol.

More, in this producing method, the alkali hydroxide is used as a base. It is desirable that the alkali hydroxide is lithium hydroxide, sodium hydroxide, or potassium hydroxide. But it is not limited to them.

More the amount of alkali hydroxide which is used in this producing method is not limited as long as it is possible to progress the reaction sufficiently.

For example, when the amount of the hydroxyl group of the above-described hydroxyflavone derivative is assumed to be 1 mol, it is desirable the amount of the alkali hydroxide is not less than 1 mol. It is more desirable that it is not less than 1 mol and not greater than 3 mol, and it is further desirable that it is not less than 1.5 mol and not greater than 2 mol.

In this producing method, it is desirable that the temperature of reaction be 10-degree centigrade or higher and 50-degree centigrade or lower, and more desirable that it be 20-degree centigrade or higher and 40-degree or lower. But it is not limited to them as far as the reaction occurs.

More, in this producing method, it is desirable that the reaction time should be not less than 1 hour and not longer than 6 hours, as long as the hydroxyl group could be substituted to a methoxy group.

If the reaction time is not less than 2 hours, it is possible to substitute the hydroxyl groups to the alkoxy groups sufficiently, and if the reaction time is not greater than 3 hours, it is possible not to waste time.

More, in this producing method, it is desirable that the separation and purification processes are performed after the above-described reaction.

As the separation and purification processes, it is possible to adopt such as filtration, partition with water or an organic solvent. But it is not limited to them.

In the alkoxyflavone derivative which is produced by this producing method, all the hydroxyl groups of the above-described hydroxyflavone derivatives are substituted to alkoxy groups. In the case of methylation, the alkoxy group is a methoxy group (—OMe), and the chemical formula is shown below.

Further, in the below-described chemical formula, the methoxy groups (—OMe) are the groups, which are changed from the hydroxyl groups of the hydroxyflavone derivatives, and the number of the methoxy groups (—OMe) is not limited to 2.

Chemical Formula 3

More, in this producing method, the examples of the alkoxyflavone derivatives include, but are not limited to, 3-alkoxyflavone, 5,7,4'-trialkoxyflavone, 5,7,3',4'-tetraalkoxyflavone, 3,5,7,4'-tetraalkoxyflavone, 3,5,7,3',4'-pentaalkoxyflavone, and 3,5,7,3',4',5'-hexaalkoxyflavone.

Therefore, by this producing method, it is possible to produce alkoxyflavone derivatives in which all the hydroxyl groups of the hydroxyflavone derivatives are substituted to alkoxy groups with a high yield.

Further, by this production method, it is possible to greatly reduce the reaction time, the amount of alkali hydroxide and solvent which is used in this method as compared with a conventional art.

The effect of this method will be confirmed in the below-described experiments.

EXAMPLES

For confirming the effect of the present invention, many examples of the embodiment of the present invention were conducted. Hereafter, the examples will be described in detail below.

Example 1

Dimethyl sulfoxide (DMSO) (8 mL) was added to powdered potassium (1.66 g, 29.7 mmol), and they were stirred at room temperature.

Quercetin (1 g, 3.3 mmol) and dimethyl sulfate were added successively to the suspension at lower than 10-degree centigrade, and the mixture was stirred at room temperature for 2 hours.

In the above reaction, the color of the suspension was changed from dark brown to light brown.

After the reaction, water (80 mL) was added, and extraction was performed three times with ethyl acetate (50 mL, 20 mL, 20 mL for each).

The ethyl acetate solution was washed by 5% sodium hydroxide aqueous solution (10 mL×4), water (10 mL×3), and brine (10 mL×1), respectively. After being dried over sodium sulfate, the ethyl acetate solution was evaporated under a reduced pressure to give a light brown solid (1.05 g).

The solid showed a single spot on thin-layer chromatography, and recrystallization from methanol afforded colorless prisms.

The melting point of the solid (147-149 degree centigrade) was the same as the value which was described in non-patent document 1.

Further, based on the NMR data described below, it was confirmed that all hydroxyl groups of the quercetin were substituted for methoxy groups.

$^1$H-NMR δ 3.88 (3H, s, OMe), 3.90 (3H, s, OMe), 3.95 (9H, s, OMe×3), 6.34 (1H, d, J=2.2 Hz, 6- or 8-H), 6.49 (1H, d, J=2.2 Hz, 6- or 8-H), 6.97 (1H, d, J=8.4 Hz, 5'-H), 7.71 (1H, dd, J=8.4, 2.0 Hz, 6'-H), 7.72 (1H, s-like, 2'-H); $^{13}$C-NMR δ 55.9, 56.1, 56.3, 56.6, 60.1, 92.7, 96.0, 109.8, 111.2, 111.8, 121.8, 123.8, 141.4, 149.0, 151.2, 152.6, 159.0, 161.3, 164.1, 174.1.

As a result of the reaction, it was confirmed that the yield was 85% and the method of the present invention was effectual.

Example 2

Dimethyl sulfoxide (DMSO) (1 mL) was added to the powdered sodium hydroxide (0.221 g, 5.5 mmol), and they were stirred at room temperature.

Quercetin (0.203 g, 0.67 mmol) and dimethyl sulfate (0.6 mL, 6.3 mmol) were added to the suspension successively at room temperature, and the mixture was stirred at room temperature for 2 hours.

After the addition of water (10 mL) the aqueous mixture was stirred for 1 hour and the insoluble material was collected by filtration. The solid material (0.166 g, 66%) was identified with the product of the above described Example 1.

Comparative Example 1

Referred to the above-described non-patent document 1 and 2, to a solution of quercetin (0.498 g, 1.7 mmol) in DMF (3.3 mL) potassium carbonate (3.4 g, 24.6 mmol) and dimethyl sulfate (0.9 mL, 7.8 mmol) were added successively at room temperature. The suspension was stirred at 70-degree centigrade for 5 hours and quenched with water.

After being acidified with 20% sulfuric acid, the mixture was extracted with ethyl acetate.

The ethyl acetate solution was dried over magnesium sulfate, and the solvent was removed. Purification of the residue (0.590 g) by preparative chromatography gave the pentamethoxy (0.30 g, 49%), the tetramethoxy (0.10 g, 18%), and trimethoxy derivatives (0.05 g, 12%).

However, as this result, it was found that the yield is insufficient in this condition.

Comparative Example 2

More, similar to the above-described Comparative Example 1, quercetin (0.202 g, 0.7 mmol) was dissolved in DMSO (1.6 mL), and potassium carbonate (0.808 g, 5.8 mmol) and dimethyl sulfate (0.55 mL, 5.8 mmol) are added successively at room temperature.

After the suspension was stirred at room temperature for 24 hours, the reaction was quenched by adding water and acidified with 20% sulfuric acid. Filtration of the insoluble material gave a residue (0.191 g).

Purification was terminated because three or more spots derived from the tetramethoxy and the trimethoxy derivatives, but not the pentamethoxy, were shown on thin-layer chromatography.

As this result, it was found that the reaction is insufficient in this condition.

Comparative Example 3

Dimethyl sulfoxide (DMSO) (4 mL) was added to powdered potassium hydroxide (0.83 g, 14.8 mmol), and the mixture was stirred at room temperature.

Quercetin (0.51 g, 1.67 mmol) and methyl iodide were added successively to the suspension at lower than 10-degree centigrade, and they were stirred at room temperature for 1.5 hours.

The reaction mixture was quenched by adding water, acidified with 20% sulfuric acid, and extracted with ethyl acetate.

The ethyl acetate solution was dried over magnesium sulfate and evaporated.

The obtained residue (0.492 g) was washed with acetone to give the pentamethoxy derivative (0.394 g).

After evaporating the acetone washings under a reduced pressure and purifying the residue by preparative chromatography, a pentamethoxy derivative 0.02 g (totally 0.418 g, 67%) was additionally obtained.

Further, by preparative chromatography, a 6-methylpentametoxy derivative (0.007 g, 1%) was obtained as byproduct.

As a result, it is found that the method which uses methyl iodide was very complicated.

Comparative Example 4

Dimethylformamide (DMF) (0.8 mL) was added to powdered potassium hydroxide (0.34 g, 5.5 mmol), and they were stirred at room temperature.

Quercetin (0.203 g, 0.67 mmol) and dimethyl sulfate (0.5 mL, 5.3 mmol) were added successively to the suspension at room temperature, and they were stirred at room temperature for 24 hours.

After the reaction was quenched by adding water and acidified with 20% sulfuric acid, the insoluble material was collected by filtration followed by washing with water.

The pentamethoxy (0.022 g, 8.9%), the tetramethoxy (0.071 g, 29%), and the trimethoxy derivatives (0.056 g, 25%) were obtained by using preparative chromatography for the obtained solid (0.181 g).

As a result, it was confirmed that the reaction and the yield were not sufficient.

INDUSTRIAL APPLICABILITY

The present invention has industrial applicability as a method of producing the alkoxyflavone derivatives.

What is claimed is:

1. A method of producing alkoxyflavone derivatives, comprising a step of reacting hydroxyflavone derivatives represented by the following Chemical Formula (1) and dialkyl sulfate in the presence of dimethyl sulfoxide and an alkali hydroxide, Chemical Formula (1)

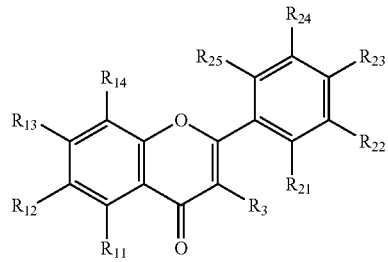

wherein $R_{11}$-$R_{14}$, $R_{21}$-$R_{25}$, and $R_3$ are each independently hydrogen, hydroxyl group, ester group, alkoxy group, alkylenedioxy group, sulfonyl group and alkyl group, and at least two of $R_{11}$-$R_{14}$, $R_{21}$-$R_{25}$, and $R_3$ are hydroxyl groups.

2. The method of producing alkoxyflavone derivatives according to claim 1,
wherein said alkali hydroxide contains at least one of lithium hydroxide, sodium hydroxide, and potassium hydroxide.

3. The method of producing alkoxyflavone derivatives according to claim 1,
wherein said hydroxyflavone derivatives contain quercetin, and said alkoxyflavone derivatives contain 3,5,7,3',4'-pentamethoxyflavone.

* * * * *